United States Patent [19]

Harris et al.

[11] Patent Number: 4,636,316
[45] Date of Patent: Jan. 13, 1987

[54] DISPOSABLE COLUMN CARTRIDGE

[75] Inventors: John Harris, Oakland; Nelson Cooke, Concord; Kristine Olsen, Richmond, all of Calif.

[73] Assignee: Beckman Instruments, Inc., Fullerton, Calif.

[21] Appl. No.: 773,501

[22] Filed: Sep. 4, 1985

Related U.S. Application Data

[63] Continuation of Ser. No. 690,564, Jan. 11, 1985, abandoned.

[51] Int. Cl.$^4$ .............................................. B01D 15/08
[52] U.S. Cl. ................................. 210/656; 210/198.2; 285/109
[58] Field of Search ........................... 210/656, 198.2; 285/109

[56]  References Cited

U.S. PATENT DOCUMENTS 3,440,864  4/1969  Blume ............................... 210/198.2
3,679,237  6/1972  De Angelis ......................... 285/109

OTHER PUBLICATIONS

The Chromapack Guide to Chromatography–General Catalog, p. 55, 1981, Chrompack Inc., Bridgewater, NJ.

Primary Examiner—John Adee
Attorney, Agent, or Firm—W. H. May; P. R. Harder

[57]  ABSTRACT

A liquid chromatographic analytical column includes an end cap that is abutted with an end edge of a holder body when the analytical column is fully inserted into a bore in the holder body. An end cap mounted to a precolumn is compressed between the end cap of the analytical column and an end nut connected to a holder union. The holder union has a central passage that admits the precolumn therethrough and a stop that engages a ferrule placed around the precolumn to compress the ferrule against the analytical column end cap to form a seal.

9 Claims, 5 Drawing Figures

DISPOSABLE COLUMN CARTRIDGE

This is a continuation of application Ser. No. 690,564, filed Jan. 11, 1985, now abandoned.

BACKGROUND OF THE INVENTION

This invention relates generally to couplers for tubes carrying highly pressurized fluids and particularly to high pressure liquid chromatography column and tube couplers. Still more particularly, this invention relates to cartridge columns for high pressure liquid chromatography.

Liquid chromatography is used for chemical analysis and for chemical product isolation or purification. A porous material is held stationary within a chamber, such as a relatively long column, and mobile liquid material is forced through the porous material. Typically the porous material is an inert powder coated with a chemically modified surface. The mobile liquid comprises a carrier liquid and other dissolved chemical substances into which a sample is injected for separation into its components. The components of the sample have have varying affinities for the porous material. Therefore, as the mobile liquid moves through a chromatographic column, the chemical substances experience delays that are functions of their affinities for the compounds stationary liquid agent.

The column separates the chemical substances into layers or zones that emerge from the column at different times. The emergence of each substance from the column is detected by a refractometer, an ultra-violet light, an absorbtometer or other suitable analytical apparatus through which the mobile liquid flows after leaving the column.

The useful life of a column may be greatly shortened by particles or chemical contaminants in the mobile liquid or in the sample input to the column. These contaminants can be trapped in a small, inexpensive precolumn connected in series upstream from the analytical column. When performance of the chromatographic system has deteriorated, the precolumn may be replaced to restore performance of the system. Previously available precolumn devices are either mechanically complex and therefore, difficult and expensive to manufacture or have deficiencies such as constrictions in the flow path that cause disturbances in the flow profile of the liquid stream.

Although it is possible to interconnect the analytical column and the precolumn with a length of capillary tubing and associated connectors, that method is expensive and introduces substantial extra mixing volume and other extra column effects. The analytical column and the precolumn are typically held within a holder body under compression by a pair of end caps. Normally capillary tubing is connected to the end caps and sealed thereto against conical seats in the ends of the end caps. The seats are subject to wear as the capillary tubing is connected and disconnected so that the end caps must be periodically replaced.

Previous high pressure liquid chromatography tubing connectors introduce radical changes in the diameter of the flow path thereby forming spaces in which fluids from one part of the stream of mobile fluid can collect and then intermix with fluids from another part of the stream. Non-uniformity in the fluid flow between the precolumn and the analytical column is undesirable because it causes eddies and stationary regions within the mobile fluid, which impair the ability of the column to separate the mobile liquid into layers. An efficient analytical column will produce narrow, symmetric bands and will cause the detecting instrument to produce a sharp peak for each substance in the mobile liquid. Previous high pressure liquid chromatography systems cause distortion in the peak shape because the edges of the layers are asymmetrical. The detector produces an output signal peak each time a substance enters the detector, indicating incomplete separation of the chemical substances when the flow path includes eddies and dead spaces.

SUMMARY OF THE INVENTION

The present invention provides a disposable cartridge column assembly that overcomes the deficiencies of previous devices and methods for forming a flow path between a liquid chromatographic analytical column and a precolumn. The present invention employs a simple, reusable ferrule seal and a direct butt connection between the analyticl column and the precolumn.

An end cap of the analytical column is abutted against an end edge of a holder body that has a central bore therethrough for receiving the tube portion of the analytical column. An end cap connected to the precolumn is abutted with the analytical column end cap to form a fluid flow path between the analytical column and the precolumn. The analytical column end cap includes a frustoconical seat around the precolumn end cap. A ferrule is placed around the precolumn end cap and compressed between the seat and a stop formed in a holder union that is threadedly engaged with the holder body. An end nut in cooperation with the end of the holder body applies a compressive force to the precolumn and the abutted end caps.

DESCRIPTION OF THE PREFERRED EMBODIMENT

Figure 1:
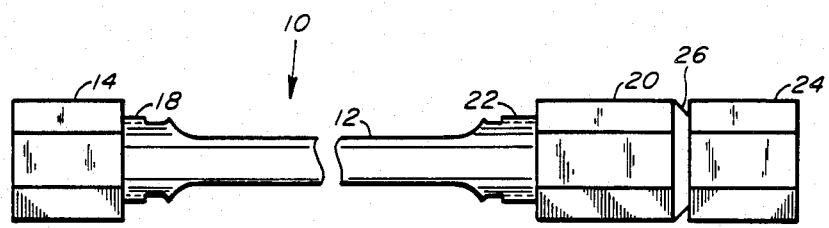
FIG. 1 is a plan view of a disposable column cartridge system according to the invention.

Referring to FIG. 1, a disposable column cartridge system 10 according to the invention includes a holder body 12 and an end nut 14 that is threadedly engaged upon an end 18 of the holder body 12. A holder union 20 is threadedly engaged upon and end 22 of the holder body 20, and a second end nut 24 that is threadedly engaged upon an end 26 of th holder union 20.

Figure 2:
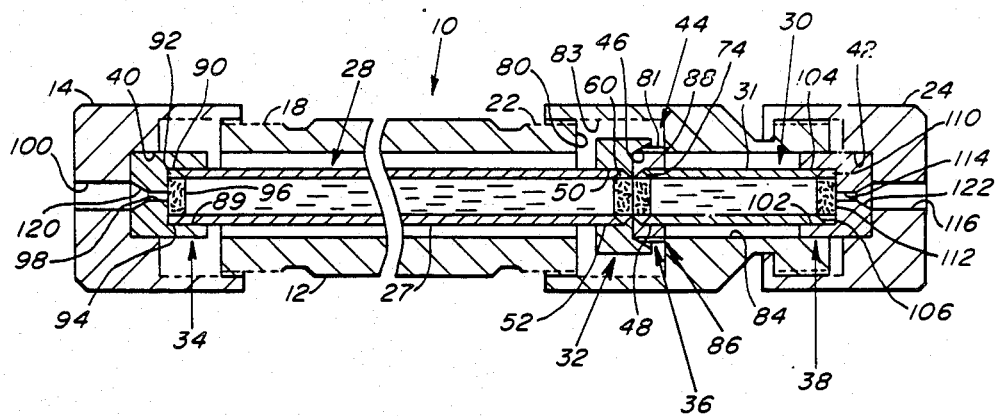
FIG. 2 is an enlarged cross sectional view of the disposable column cartridge system of FIG. 1 showing an analytical column, a precolumn and apparatus for maintaining a fluid flow path between the precolumn and the analytical column and the precolumn.
Figure 3:
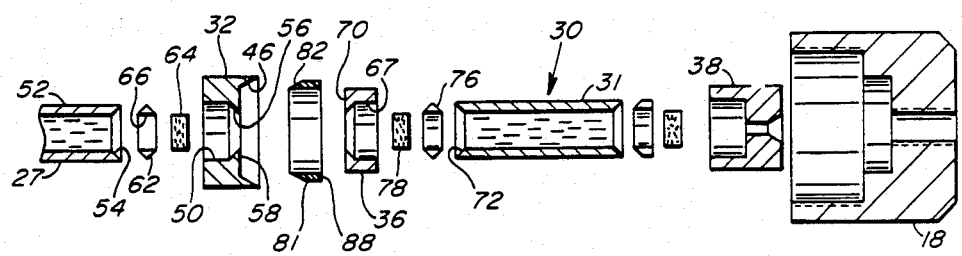
FIG. 3 is an exploded cross sectional view of a portion the apparatus of FIG. 2.
Figures 4, 5:
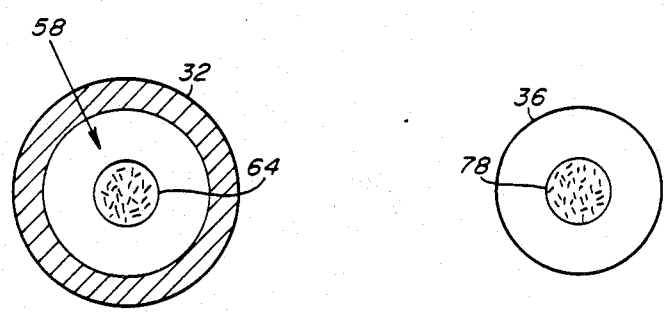
FIG. 4 is an enlarged end view of an end cap included in the analytical column shown in FIGS. 2 and 3.
FIG. 5 is an enlarged end view of an end cap included in the precolumn shown in FIGS. 2 and 3.

Referring to FIGS. 2 and 3, the disposable column cartridge system 10 includes an analytical column 28 and a precolumn 30 that are held in axial alignment in the holder body 12. The analytical column 28 includes a tube 27 and first end cap 32 and a second end cap 34 mounted to the tube 27. The precolumn 30 includes a tube 31 and a pair of end caps 36 and 38 mounted thereto. The end cap 34 is retained within a void 40 in the end nut 14, and the end cap 38 is retained within a void 42 in the end nut 24. The end cap 32 includes an end 44 having a void 46 therein. When the disposable column cartridge system 10 is assembled as shown in FIG. 2, the end cap 36 has a portion 48 that fits within the void 46, which preferably has a frustoconical configuration with the narrower end of the frustocone being inside the end cap 32.

Referring to FIGS. 2 and 3, the end cap 32 includes a first hollow cylindrical bore 50 that is press fitted upon an end 52 of the tube 27. The outermost portion of the end 52 defines a frustoconical portion 54 that tapers into the interior of the tube 27 such that the narrower end of the frustoconical portion 54 has substantially the same diameter as the bore 50. The wider end of the frustoconical portion 54 is substantially the same diameter as the outer diameter of the tube 27. The end cap 32 defines a frustoconical portion 56 that has its narrower end at a surface 58 thereof. The frustoconical portion 56 widens away from the surface 58 such that the wider end of the frustoconical portion 56 is inside the passage 50. When the end cap 32 is press fitted upon the analytical column 28, the wider ends of the frustoconical portions 54 and 56 are adjacent. The end 52 abuts the wider portion of the frustoconical portion 56, which acts as a stop to limit penetration of the tube 27 into the cavity 50.

The frustoconical portion 54 may be formed by machining the end 52 of the tube 27, and the frustoconical portion 56 may be formed by machining the bore 50 to be suitably tapered at the end that abuts the end 52 of the analytical column 28.

When the disposable cartridge column system 10 is fully assembled, the two frustoconical portions 54 and 56 cooperate to enclose a volume 60 that is essentially a ring having a triangular cross section. A filter border 62 is retained within the region bounded by the frustoconical end 54 of the analytical column 28 and the frustoconical portion 56 of the end cap 32. A filter 64 is retained within a cylindrical region 66 inside the filter border 62.

The end cap 36 includes a generally cylindrical cavity 67 into which an end 68 of the tube 31 is press fitted. The cavity 67 terminates in a frustoconical portion 67 that has its wider end inside the end cap 36 and its narrower end adjacent a surface 70 of the end cap 36. The end 68 of the tube 31 defines a frustoconical volume 72 that is similar to the frustoconical volume 54 in the end 52 of the tube 27. The frustoconical volume 72 is configured such that the narrower end thereof is inside the tube 62. When the disposable cartridge column system 10 is assembled, the wider end of the frustoconical volume 72 is adjacent the wider end of the frustoconical portion 67 of the end cap 36. The juncture of the end cap 36 and the wider end of the frustoconical volume 72 functions as a stop to limit penetration of the tube 31 into the end cap 36. When the end cap 36 and the tube 31 are properly connected together as best shown in FIG. 2, the frustoconical portions 67 and 72 cooperate to enclose a volume 74 that is formed as a ring having a triangular cross section.

A filter border 76 that is preferably substantially identical to the filter border 62 is placed inside the cavity 66 before insertion of the tube 31. The filter border 76 is therefore retained within the volume 74 bounded by the frustoconical portions 67 and 72. A filter 78, which is substantially identical to the filter 64 is placed in a cylindrical cavity 80 in the filter border 76.

The end cap 36 fits within the cavity 46 and the end cap 32 is positioned within the holder union 20 spaced apart from the end edge 80 of the holder body 12. A ferrule 81 is placed around the end cap 36. The ferrule preferably has a frustoconical portion 82 that narrows toward the abutment of the end caps 32 and 36. The holder union 20 includes a threaded bore portion 83 and a smooth bore portion 84 having a diameter less than that of the threaded portion 83. The intersection of the bore portions 83 and 84 defines a stop 86 that engages an end 88 of the ferrule 81. The cavity 46 preferably has a frustoconical wall portion 86 that abuts the frustoconical portion 82 of the ferrule 81. Advancing the holder union 20 upon the threaded end of the holder body 12 compresses the ferrule 81 against the cavity wall 86 to form a seal around the abutment of the end caps 32 and 36.

The end cap 34 includes a bore 88 that fits closely upon an end 90 of the tube 27. The end 90 has a frustoconical portion 92 therein for receiving a filter border 94, which surrounds a filter 96. A passage 98 extends through the end cap 34 in alignment with a passage 100 in the end nut 14.

The end cap 38 includes a bore 102 that fits closely upon an end 104 of the tube 31. The end 104 has a frustoconical portion 106 therein for receiving a filter border 110, which surrounds a filter 112. A passage 114 extends through the end cap 38 in alignment with a passage 116 in the end nut 24.

The end cap 38 projects through the bore portion 84 to fit within a recess 116 within the end nut 24. Advancing the end nut 24 upon the threaded end 26 of the holder union compresses the precolumn 30 and the analytical column 28 between the two end caps 14, 24. The compressive force must be sufficient to maintain the analytical column 28 and the precolumn 30 properly positioned within the holder body 12. However, the compressive force should held to a value that will not buckle the analytical column 28. The liquid pressure inside the fluid flow path between the precolumn and the analytical column 27 may be as much as approximately 8000 psi. In order to contain a pressurized fluid, the sealing force on the ferrule 81 against the conical seat 86 must be at least as great as the force the pressurized liquid creates on the ferrule. The sealing force may be as great as several hundred pounds in some high pressure applications.

The end caps 34 and 38 preferably include frustoconical seats 120 and 122, respectively, in their outer ends for forming seals with capillary tubing connectors (not shown) that are ordinarily used to connect the column cartridge system 10 to other apparatus (not shown). Therefore, when the seats 120, 122 become worn, it is not necessary to replace the end caps 14, 24, as is required in the prior art.

The end caps 32, 34, 36 and 38, the end nuts 14, 24 and the tubes 27, 31 are preferably formed of 316 stainless steel. The ferrule 81 is preferably formed of a polyimide plastic material sold by E.I. DuPont under the trademark "Vespel". The filters 38 and 78 are preferably formed of fritted disks of Hastelloy C, and the borders 36 and 76 are preferably formed of a fluoropolymeric material such as CTFE, which 3M Company sells under the trademark "KEL-F".

What is claimed is:

1. A liquid chromatography cartridge column system comprising:

an analytical column having an analytical column bore;

a precolumn having a precolumn bore;

a holder body having a bore therein;

a first end cap mounted upon a first end of the analytical column;

a second end cap mounted upon a first end of the precolumn, the second end cap having a portion formed to abut the end of the first end cap, so that the analytical column and the precolumn are axially aligned and abutting each other to form a fluid flow path between the analytical column bore and the precolumn bore;

a ferrule positioned around the second end cap;

means for compressing an end of the ferrule against the first end cap; and means for urging the precolumn and the first end cap toward the end of the holder body.

2. The liquid chromatography cartridge column system of claim 1 wherein the means for compressing an end of the ferrule against the first end cap comprises:

a threaded portion on the holder body proximate the holder body end; and a holder union in threaded engagement with the threaded portion of of the holder body, the holder union including a passage for admitting the precolumn therethrough and a stop for engaging the ferrule, the ferrule being compressed between the end of the holder body and the stop as the holder union is advanced along the threaded portion of the holder body.

3. The liquid chromatography cartridge column system of claim 1 wherein the means for urging the precolumn and the first end cap toward the end of the holder body includes:

a second threaded portion on the holder union; and an end nut formed for threaded engagement with the second threaded portion of the holder union, the end nut including a cavity therein for receiving a second end of the precolumn, the precolumn being compressed between the first end cap and the end nut as the end nut is advanced into threaded engagement with the holder union.

4. The liquid chromatography cartridge column system of claim 3 wherein the means for compressing an end of the ferrule against the first end cap comprises:

a threaded portion on the holder body proximate the holder body end; and a holder union in threaded engagement with the threaded portion of of the holder body, the holder union including a passage for admitting the precolumn therethrough and a stop for engaging the ferrule, the ferrule being compressed between the end of the holder body and the stop as the holder union is advanced along the threaded portion of the holder body.

5. The liquid chromatography cartridge column system of claim 4, further comprising a cavity formed in the end of the first end cap for receiving the second end cap therein to align the analytical column tube and the precolumn tube and for providing a seat for an edge of the ferrule to form a seal.

6. A method for forming a high pressure seal around a fluid path formed by abutting a first end cap mounted to a chromatographic analytical column and a second end cap mounted to a precolumn, comprising the steps of:

forming a bore in a holder body, the bore having a diameter less than the diameter of the first end cap;

inserting the analytical column in the bore such that the first end cap abuts and an end edge of the holder body;

abutting the first and second end caps;

placing a ferrule around the second end cap;

urging the ferrule toward an end of the first end cap; and compressing the precolumn between an end nut and the end of the first end cap.

7. The method of claim 6, further including the steps of:

forming a cavity in the end of the first end cap to provide a seat for the ferrule; and compressing the ferrule against the seat.

8. A liquid chromatography cartridge column system comprising:

an analytical column having an analytical column bore;

a precolumn having a precolumn bore;

the cross-sectional inner diameter of the analytical column bore and the precolumn bore being equal;

a first end cap mounted upon a first end of the analytical column;

a second end cap mounted upon a first end of the precolumn, the second end cap having a portion formed to abut the end of the first end cap, so that the analytical column and the precolumn are axially aligned and abutting each other to form a fluid flow path between the precolumn and the analytical column;

the analytical column having a first and second liquid filter positioned at each end, each of said filters being telescoped within said analytical column bore so that the outer diameter of said filters is at least equal to the diameter of said analytical column bore;

the precolumn having a third and fourth liquid filter positioned at each end, each of said filters being telescoped within said precolumn bore so that the outer diameter of said filters is at least equal to the diameter of said precolumn bore;

the analytical column and the precolumn being juxtaposed end to end so that the third filter of the precolumn is positioned in axial alignment with the second filter of the analytical column;

the liquid filters of the analytical column and the precolumn being secured by at least one end cap, each end cap positioned at the ends of each column;

each end cap having an outer diameter greater than the column to which it is affixed so that the column is telescoped within the inner diameter of the end cap and;

each end cap having an inner abutment shoulder for receiving the liquid filters and providing a seat for securing each filter in abutment against said shoulder on one side of each filter and against the tubular body of the column on the other side of each filter, so that the precolumn and the analytical column form a uniform flow path through the equal inner diameters of the columns.

9. The liquid chromatography cartridge system of claim 8, wherein a set of capillary tubing connectors surrounding a set of capillary tubes are positioned at each end of said liquid chromatography cartridge system, the cartridge system further including a third end cap of the precolumn, opposite said second end cap, mounted on the second end of the precolumn, and a fourth end cap mounted on the analytical column, opposite the first end cap, the third and fourth end caps having frustoconical seats for receiving and sealingly engaging capillary tubing connectors.

* * * * *